(12) United States Patent
Vesnaver

(10) Patent No.: US 6,788,978 B2
(45) Date of Patent: Sep. 7, 2004

(54) SANITARY ARTICLE TO BE WORN IN CONTACT WITH THE SKIN, ADAPTED TO PROVIDE METALLOTHERAPY EFFECTS

(75) Inventor: Giuliano Vesnaver, Medole (IT)

(73) Assignee: Gafitex S.r.l., Guidizzolo (IT)

( * ) Notice: Subject to any disclaimer, the term of this patent is extended or adjusted under 35 U.S.C. 154(b) by 196 days.

(21) Appl. No.: 09/967,962

(22) Filed: Oct. 2, 2001

(65) Prior Publication Data

US 2002/0169479 A1 Nov. 14, 2002

(30) Foreign Application Priority Data

May 9, 2001 (IT) ..................................... MI20010260 U

(51) Int. Cl.7 ................................................. A61N 1/04
(52) U.S. Cl. ........................... 607/115; 607/2; 607/144
(58) Field of Search ........................... 607/1, 2, 46, 75, 607/115, 142, 144, 148, 149

(56) References Cited

U.S. PATENT DOCUMENTS

| | | | | |
|---|---|---|---|---|
| 559,254 A | * | 4/1896 | Blair | 607/144 |
| 683,098 A | * | 9/1901 | Baecker | 607/115 |
| 700,915 A | * | 5/1902 | Harmel | 607/115 |
| 4,061,557 A | * | 12/1977 | Nishizawa et al. | 204/277 |
| 4,653,473 A | * | 3/1987 | Kempe | 128/846 |
| 4,706,672 A | | 11/1987 | Jones | |
| 5,038,796 A | * | 8/1991 | Axelgaard et al. | 607/152 |
| 6,014,585 A | * | 1/2000 | Stoddard | 607/2 |

FOREIGN PATENT DOCUMENTS

| | | | |
|---|---|---|---|
| CH | 666 993 | 9/1988 | |
| DE | 28 40 175 | 3/1980 | |
| DE | 35 03 891 | 9/1985 | |
| RU | 2139109 | * 10/1999 | A61N/1/18 |

OTHER PUBLICATIONS

Patent Abstracts of Japan, vol. 1996, No. 3, Mar. 29, 1996 & JP 07 299152 A (Unitika Ltd), Nov. 14, 1995 *abstract*.

* cited by examiner

Primary Examiner—Jeffrey R. Jastrzab
(74) Attorney, Agent, or Firm—Guido Modiano; Albert Josif; Daniel O'Byrne

(57) ABSTRACT

A sanitary article to be worn in contact with the skin of a user that is adapted to provide metallotherapy effects, comprising a knitted part that has, at least on a side thereof adapted to be directed toward the user's skin, rows of knitting or portions of rows of knitting formed by yarns that comprise a metal or metalloid adapted to provide metallotherapy effects.

10 Claims, 1 Drawing Sheet

SANITARY ARTICLE TO BE WORN IN CONTACT WITH THE SKIN, ADAPTED TO PROVIDE METALLOTHERAPY EFFECTS

BACKGROUND OF THE INVENTION

The present invention relates to a sanitary article to be worn in contact with the skin, adapted to provide metallotherapy effects.

The theory on which metallotherapy is based likens the human body to a voltaic pile, starting from the observation that if a plate of positive metal (for example copper) is applied to the spinal region and a plate of negative metal (for example zinc) is applied to the region of the abdomen, and if these two plates are connected to the two poles of a microammeter, current is observed to flow between the two plates, i.e., through the human body.

By interconnecting the two plates with an electrically conducting wire, a short-circuit is produced in the human body together with an ionization whose result is the penetration of ions of the positive metal in the body of the subject.

This penetration can still occur, albeit more slowly and to a lesser extent, if the plates are not connected electrically to each other.

The metallic trace elements that penetrate the body act on the terminations of the autonomic system, struck by spasm, which can be ascribed to cloggings (flocculates) of leukocytes that obstruct capillaries, and are able to cause consequently a relaxation of the spasm, eliminating the white cells that are dead or liquefied in general circulation.

Substantially, according to this theory, the application of positive and negative metals to the surface of the skin generates an infinitesimal current that is capable of healing or improving certain deficits or chronic functional or nervous disorders in which acidosis is the norm. The basic concept is that the human body, its tissues, its humors are used as the liquid or compound of a dry cell, converting the body, with the two metals (positive and negative), into a veritable voltaic pile.

It should be noted that the "human pile", whose living electrolyte is more or less acid, operates accordingly, actively or not, depending on its individual acidity. Accordingly, the resulting intracellular current is able to self-regulate, since its intensity depends on organic acidosis.

The effects that can be obtained by metallotherapy are:
general stimulation of the body;
stimulation of the nutritional function;
natural and spontaneous elimination of organic residues and flocculates;
improvement of blood circulation;
cessation of various pains;
recovery of nervous energy.

In particular, the use of the copper-zinc combination prevents the onset of rheumatic pains and reduces stress states of the emotional type. The use of silicon eliminates excessive perspiration yet keeps the skin elastic and soft without making it dry.

SUMMARY OF THE INVENTION

Starting from this theory, the aim of the present invention is to provide a sanitary article to be worn in contact with the skin that is adapted to provide metallotherapy effects.

Within this aim, an object of the invention is to provide a sanitary article that can be produced with knitting machines or hosiery knitting machines of a conventional type.

Another object of the invention is to provide a sanitary article that can be manufactured at competitive costs.

This aim and these and other objects that will become better apparent hereinafter are achieved by a sanitary article to be worn in contact with the skin of a user that is adapted to provide metallotherapy effects, comprising a knitted part, wherein said part has, at least on a side thereof adapted to be directed toward the user's skin, rows of knitting or portions of rows of knitting formed by yarns that comprise a metal or metalloid adapted to provide metallotherapy effects.

BRIEF DESCRIPTION OF THE DRAWINGS

Further characteristics and advantages of the present invention will become better apparent from the following detailed description of a sanitary article according to the invention, illustrated only by way of non-limitative example in the accompanying drawings, wherein.

DESCRIPTION OF THE PREFERRED EMBODIMENTS

Figure 1:
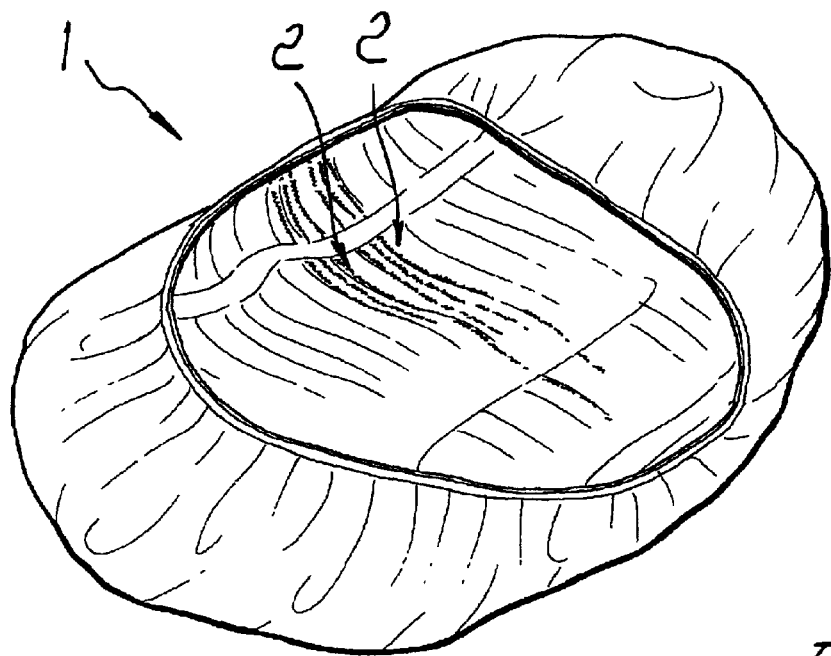
FIG. 1 is a perspective view of a sanitary article according to the invention, constituted by a footlet.
Figure 2:
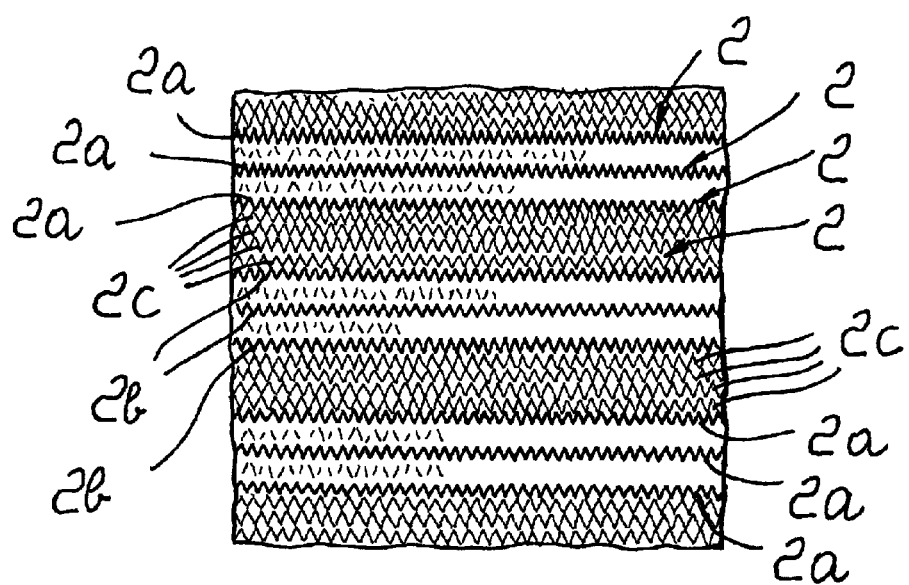
FIG. 2 is an enlarged-scale view of a portion of the knitted part that constitutes the sanitary article according to the invention.

With reference to the figures, the sanitary article according to the invention, which in the illustrated embodiment is constituted by a footlet generally designated by the reference numeral 1, comprises a knitted part that has, at least on its side adapted to be directed toward the user's skin, rows of knitting 2 or portions of rows of knitting that are produced with yarns that comprise a metal or metalloid adapted to provide metallotherapy effects.

The metal or metalloid can be provided in yarn form, so that it can be knitted directly to form the rows of knitting 2 or portions of rows, or can be embedded, in the form of powder or fibers or particles, in the natural or synthetic fibers of a yarn used to form the rows 2 or row portions.

The metals or metalloids of the yarns that compose the rows 2 or row portions are preferably constituted by copper and/or zinc and/or silicon.

The rows of knitting 2 or portions of rows of knitting made of such materials are preferably mutually spaced transversely to the direction in which the rows of knitting are arranged and are alternated and meshed with rows of knitting 3 formed with natural or synthetic yarns.

Conveniently, there are at least two types of row of knitting 2 or portions of rows, produced with yarns comprising metals or metalloids having a metallotherapeutic effect, which are different from each other and alternated transversely to the extension rows of the knitted part.

For example, it is possible to provide two types 2a, 2b of rows 2 or row portions, formed respectively by means of copper yarns and zinc yarns. On the knitted part there are rows 2a, 2b made of such metals, alternated and meshed with rows made of natural and synthetic yarns. Considering only the rows of knitting formed with yarns made of these metals, and moving along the knitted part transversely to the extension of each individual row, there are rows 2a or row portions made of copper alternated with rows 2b or row portions made of zinc.

Depending on the metallotherapeutic effect to be obtained, it is also possible to provide different types of rows or row portions formed with yarns that comprise a metal or metalloid, for example three types of row 2a, 2b, 2c, respectively formed with copper yarns, zinc yarns and yarns containing silicon, alternated and meshed with rows made of natural or synthetic yarns, and alternated with each other.

Optionally, instead of providing individual rows 2 or row portions, made of yarns comprising metals or metalloids adapted to provide metallotherapy effects, it is possible to provide groups of rows 2 or row portions meshed with each other and with the rows of knitting made of natural or synthetic yarns that are contiguous.

In the illustrated embodiment, the sanitary article is constituted by a footlet, but it might be constituted, obviously with another shape, by a sock or by an elastic bandage such as a wrist bandage, ankle bandage, knee bandage, body belt, protective bandage for the shoulders or the like.

In using the sanitary article according to the invention, the metals or metalloids of which the rows 2 or row portions are made, by being in contact with the user's skin, achieve the above-described effects of metallotherapy. Moreover, since this is an article constituted by a knitted part, the metals or metalloids that have metallotherapeutic effects are kept constantly in contact with the user's skin without causing any discomfort.

In the particular case in which the article according to the invention is constituted by a sock or footlet, by virtue of the combined action of copper, zinc and silicon it is possible to achieve beneficial effects at the local level as regards blood circulation, prevention or reduction of joint pains or rheumatic pains, regularization of perspiration and, at the systemic level, as regards the reduction of stress states of the emotional type.

In practice it has been observed that the sanitary article according to the invention fully achieves the intended aim and objects, since by virtue of the rows of knitting comprising metals or metalloids it achieves metallotherapy effects on the user.

Another advantage of the article according to the invention is that it performs a constant metallotherapeutic activity without causing any discomfort to the user.

The disclosures in Italian Utility Model Application No. MI2001U000260 from which this application claims priority are incorporated herein by reference.

What is claimed is:

1. A sanitary article to be worn in contact with the skin of a user that is adapted to provide metallotherapy effects, comprising a knitted part, wherein said part has, at least on a side thereof adapted to be directed toward the user's skin, rows of knitting or portions of rows of knitting made of yarns that comprise silicon and at least one (a) metal (or metalloid) adapted to provide metallotherapy effects.

2. The sanitary article according to claim 1, wherein said rows of knitting or portions of rows of knitting, formed with yarns comprising silicon and at least one (a) metal (or metalloid) adapted to provide metallotherapy effects, are mutually spaced transversely to an extension of the rows of knitting in the knitted fabric of the part.

3. The sanitary article according to claim 1, wherein said rows of knitting or portions of rows of knitting comprise at least two types of row or row portion that alternate transversely to an extension of the rows of the knitted part each type of row or row portion being formed with a yarn that comprises at least one metal (a or metalloid) that is adapted to provide metallotherapy effects and is different from the metal or of the yarn of the rows of knitting or portions of rows of knitting of the other type or types of row or row portion.

4. The sanitary article according to claim 1, wherein said rows of knitting or portions of rows of knitting formed with yarns comprising silicon and at least one (a) metal (or metalloid) adapted to provide metallotherapy effects are meshed and alternated with rows of knitting (3) made of natural or synthetic yarns.

5. The sanitary article according to claim 1, wherein said at least one metal (or metalloid) is constituted by copper.

6. The sanitary article according to claim 1, wherein said at least one metal (or metalloid) is constituted by zinc.

7. The sanitary article according to claim 1, wherein said at least one metal (or metalloid) is embedded in a yarn of natural or synthetic fiber.

8. The sanitary article according to claim 1, wherein said article is a footlet.

9. The sanitary article according to claim 1, wherein said article is a sock.

10. The sanitary article according to claim 1, wherein said article is an elastic bandage, including a wrist bandage, ankle bandage, knee bandage, body belt, shoulder protection bandage or the like.

\* \* \* \* \*